United States Patent [19]

Rider

[11] Patent Number: 5,062,419
[45] Date of Patent: Nov. 5, 1991

[54] NEBULIZER WITH VALVED "T" ASSEMBLY

[76] Inventor: Donald L. Rider, 25 Chianti, Reno, Nev. 89512

[21] Appl. No.: 637,907

[22] Filed: Jan. 7, 1991

[51] Int. Cl.[5] .......................... A61M 11/00

[52] U.S. Cl. .......................... 128/200.21; 128/200.14

[58] Field of Search .......................... 128/200.14, 200.18, 128/200.21, 203.12, 205.12

[56] References Cited

U.S. PATENT DOCUMENTS

| | | | |
|---|---|---|---|
| 3,580,249 | 5/1971 | Takaoka | 128/200.14 |
| 3,658,059 | 4/1972 | Steil | 128/200.21 |
| 3,826,255 | 7/1974 | Havstad et al. | 128/194 |
| 3,874,379 | 4/1975 | Enfield et al. | 128/200.18 |
| 3,903,884 | 9/1975 | Huston et al. | 128/200.18 |
| 4,231,973 | 11/1980 | Young et al. | 261/78 A |
| 4,251,033 | 2/1981 | Rich et al. | 239/338 |
| 4,333,450 | 6/1982 | Lester | 128/200.14 |
| 4,560,519 | 12/1985 | Cerny | 261/78 A |
| 4,746,067 | 5/1988 | Svoboda | 239/338 |
| 4,792,097 | 12/1988 | Kremer, Jr. et al. | 128/200.18 |
| 4,805,609 | 2/1989 | Roberts et al. | 128/200.21 |

*Primary Examiner*—Edgar S. Burr
*Assistant Examiner*—Lisa E. Malvaso
*Attorney, Agent, or Firm*—Sughrue, Mion, Zinn Macpeak & Seas

[57] ABSTRACT

A horizontally elongated, shallow, hollow nebulizer body has vertically spaced horizontal top and bottom walls. The bottom wall is of much shorter length. The horizontal bottom wall is of relatively short length and terminating at the side opposite of a vertical side wall, in an upwardly oblique bottom wall portion extending to the end of the horizontal top wall remote from said vertical end wall. The nebulizer chamber produced thereby drains in the direction of the short length horizontal bottom wall of the hollow body. A horizontal source gas supply tube extends through the vertical end wall of the nebulizer body, and connects to a vertically upright pipe terminating in a reduced diameter nozzle opening. An inverted cup-like hollow cylindrical nozzle member is mounted concentrically about the vertical pipe, has an internal diameter in excess of the outside diameter of the short vertical pipe to form a liquid aspirating passage leading to a mixing chamber at the upper end of the short vertical pipe. A medication injection port is formed by a short length horizontal pipe integral with the nebulizer body end wall. A valved T tube assembly is fixedly mounted to the top wall of the nebulizer to the side of that body remote from the inverted cup-shaped nozzle member and is open to the nebulizer chamber to receive selectively, depending upon valve setting, the source gas and a liquid medication in fine mist particle form for selective feed to the interior airways of a patient via an otherwise conventional ventilator circuit.

12 Claims, 2 Drawing Sheets

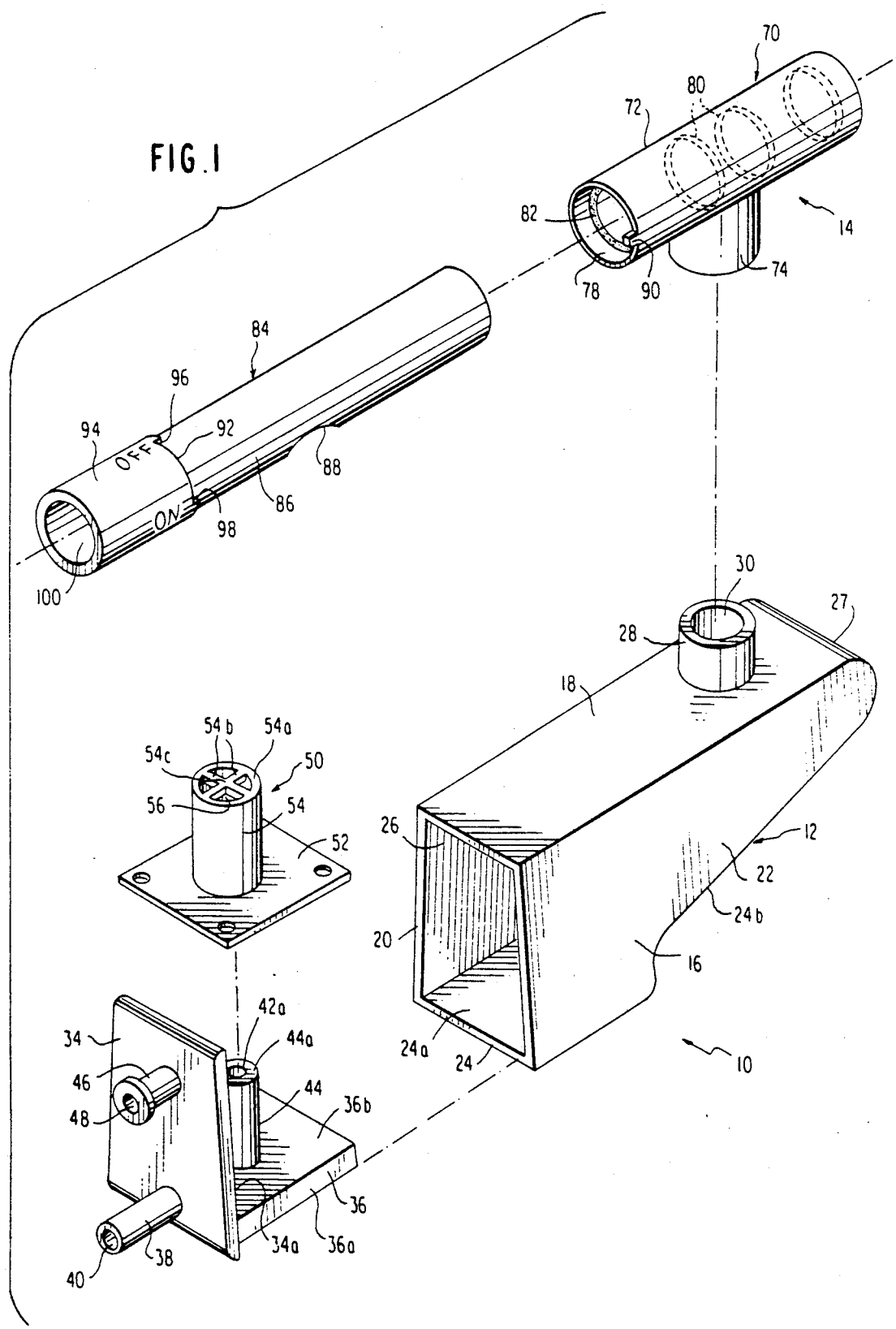

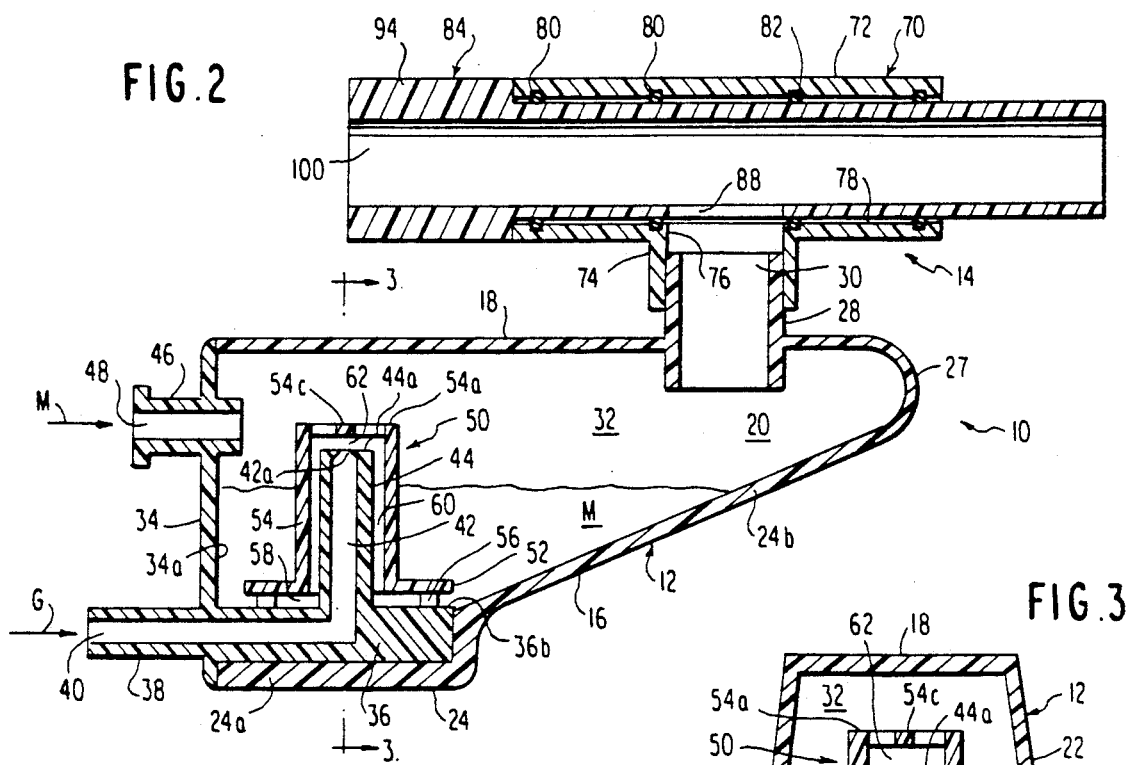

NEBULIZER WITH VALVED "T" ASSEMBLY

FIELD OF THE INVENTION

This invention relates to a new and improved pneumatic nebulizer with attached valved "T" assembly, that is particularly suited to deliver medications to patients that are ventilator dependent. However, it may be used in other applications to nebulize liquids to a particulate size.

BACKGROUND OF THE INVENTION

The history of the nebulize has been well documented. The nebulizer is a pneumatic, or electric powered device that nebulizes medications, at a particulate droplet size, to be delivered through an opening in the top of the nebulizer into a "T" which is attached at each end into the ventilator circuit. The medication is then mixed and delivered through the ventilator tubing, or circuit, into the interior airways of the patient. The particle size of the delivered medication is important and should be of correct size for better distribution throughout the airways. If the particles (droplets) of medication are too large they will be delivered to the interior of the trachea and upper airways. If the particulate droplets are too small they will be exhaled. If the correct size droplets are distributed throughout the bronchial tree, the patient will be benefitted.

Many different nebulizers, commonly called hand held nebulizers, are commercially available. They hold up to 10cc's of medication. They include an elongated body three and one half inches long and are used in a vertical position. An unvalved "T" is attached to the top of the nebulizer which can be coupled into the ventilator circuit. The source gas entry tubing is vertically inserted into the bottom of the nebulizer. The device from the top of the "T" to the bottom of the source gas connector may be up to 6 inches in height. Such nebulizers are used in ventilator circuits and medication added by unscrewing the cap from the bowl and injecting the medication into the bowl, or by removing the "T" from the top of the nebulizer body and injecting the medications into the bowl. The cap or "T" is then replaced on the nebulizer. The ventilator circuit is then disconnected proximal to the patient on the inspiratory side of the circuit. The nebulizer is placed into the circuit by connecting the disconnected tubing of the circuit to the end of the "T", and the other end of the "T" is attached to a six inch piece of tubing that is then attached proximal to the patient at a patient "Y". The nebulizer is then started and the medications are nebulized and delivered through the top of the nebulizer into the ventilator circuit. The medication in small particle size droplets is picked up by the gas of the inspiratory phase of the ventilator cycle and delivered into the airways.

Drawbacks of the commercially available nebulizers are that most are designed to be used in a vertical position or slightly tilted from vertical position in the ventilator circuit. When this position is not maintained all of the medication is not nebulized. A portion of the medication remains in the nebulizer bowl. Further, the source gas tubing entering the bottom of the nebulizer vertically often kinks off due to the weight of the circuit structure pushing down on the nebulizer, which nebulizer often rests on the patient's chest or shoulder. When the tubing of the source gas kinks off, the gas flow is reduced. Poor or no nebulization of the medication results. Further, the height of the device, when inline, in the ventilator circuit makes it hard to place the nebulizer proximal to the patient. With a six inch piece of tubing placed between the nebulizer and the patient, the six inches of extra tubing creates rainout of medication into the tubing. A portion of the medication never reaches the interior of the airways and is of no benefit.

A further drawback is that each time the patient needs medication nebulized, the ventilator circuit is disconnected from the patient. The nebulizer is placed in line and the ventilator circuit reconnected. Medication is nebulized. The nebulizer is thereafter taken out of the circuit and the circuit is then, again reconnected. The nebulizer is put away until its next use.

Patients receive medications in this manner from 4 to 24 times each day. Each time the ventilator circuit is disconnected depressurization occurs which compromises the oxygen blood levels of the patient who is being supported with positive end expiratory pressure (PEEP). PEEP is pressure constantly used in the circuit to keep the alveoli open for gas exchange to occur in the terminal airways of the patient's lungs. Further, each time the circuit is opened to the atmosphere to place the nebulizer inline, or to remove it, contamination of the ventilator circuit and the nebulizer can occur.

A further drawback is that if the nebulizer is left in the circuit it will fill with water from condensation in the tubing and the water would have to b drained therefore before the nebulizer could be used.

A further drawback during emergencies is that when patients are being ventilated with a resuscitation bag, cardiac medications are delivered via the intubation tube into the lungs for faster effect to the heart. Currently nebulizers with "T"s are too cumbersome to nebulize heart medications during resuscitation.

A further drawback exists. In recent years the use of continuous nebulized medication has been found to be beneficial in treating some patients with lung disease. Currently most nebulizers have to be adapted to permit their use for continuous nebulization as they do not have a medication port that can be connected to IV tubing.

SUMMARY OF THE INVENTION

The new and improved PEEP "T" Nebulizer of this invention has been designed to satisfy the drawbacks of previously designed nebulizers.

An object of this invention is to provide a new and improved nebulizer with attached valved "T" to nebulize medication or liquid at an appropriate controlled particle droplet size delivered through a communication in the top of the nebulizer body into the valved PEEP "T", mixed with the gas in the ventilator circuit and delivered to the interior of the airways. The invention uses a horizontal nebulizer body which reduces the height of the body to three and one half inches from the top of the "T" to the bottom of the nebulizer. This allows the nebulizer to be placed inline in the ventilator circuit without the need for a six inch extension tubing. Thus the nebulizer is proximal to the patient. Less rainout of medication in the tubing occurs and more medication is delivered to the patient's airways. The nebulizer source gas tubing connects to the nebulizer horizontally thus preventing the tubing from kinking and shutting off flow to the nebulizer. The inclination of the bottom wall of the nebulizer body insures that nebulizing of substantially all of the medication occurs for many different angles of inclination of the body. A medication injection port on the back of the nebulizer allows the PEEP "T" nebulizer to remain in the ventilator circuit. maintaining the integrity of the circuit so that PEEP is maintained at all times. There is less chance of contamination, because there is no requirement to open the circuit to place the nebulizer inline or, remove it from the circuit. Further the medication injection port allows a connection to be made to a continuous medication feed system. The valved PEEP "T" prevents condensation from draining water back into the nebulizer and filling up the medication chamber and may be connected to a resuscitation bag to be used with the small horizontal nebulizer body to nebulize heart medications for faster effect on the heart.

BRIEF DESCRIPTION OF THE DRAWINGS

FIG. 1 is an exploded perspective view of a nebulizer with a valve "T" assembly forming a preferred embodiment of the invention.

FIG. 2 is a vertical, longitudinal sectional view of the nebulizer of FIG. 1.

FIG. 3 is a vertical, sectional view of the nebulizer body taken about line 3—3 of FIG. 2.

FIG. 4 is a perspective view of an alternate form of a valved PEEP "T" assembly for mounting to the nebulizer body.

FIG. 5 is a longitudinal sectional view of "T" assembly of FIG. 4.

DESCRIPTION OF THE PREFERRED EMBODIMENTS

The improved, nebulizer with a valved PEEP "T" assembly is indicated generally at 10 in FIGS. 1 and 2, and consists principally of two components, a nebulizer body indicated generally at 12, and a valved PEEP "T" assembly indicated generally at 14.

The nebulizer body 12, may be formed of molded plastic as may most of the components of the nebulizer 10. The nebulizer body 12 is of horizontal elongated form consisting of an open ended molded plastic casing 16 having, integrally, a generally flat, horizontal top wall 18, laterally opposed, upwardly and inwardly oblique sidewalls 20 and 22, and a bottom wall 24 having a short, flat portion 24*a* which, extends only a short distance from open end 26 of casing 16 and which flat, horizontal bottom wall 24*a* has extending, therefrom, away from open end 26, a unitary upwardly oblique bottom wall portion 24*b*. The top wall 18 and the oblique bottom wall portion 24 merge into a small vertical height arcuate end wall 27. Further, integrally molded into the top wall 18 is a vertically upright cylindrical outlet tube 28 forming an outlet passage or opening 30 for the nebulizer chamber 32. The open end 26 of casing 16 is closed by a vertical end wall 34, which may be adhesively fixed and sealed to casing 16 about the ends of bottom wall 24 laterally opposed side walls 20. 22 and top wall 18 of that member. End wall 34 is of trapezoidal plan form. The end wall 34 has on the surface 34*a* facing opening 26, an integral, horizontally projecting base 36 of rectangular parallelepiped form. Base 36 has opposite sloped sides 36*a* which match the oblique inclination of laterally opposed side walls 20. 22 of casing 16 and the base is insertably received within the interior of the casing 16. Further, a source gas supply tube 38 is integrally molded with end wall 34, having a bore 40 of relatively small diameter, which bore 40 extends through the wall 34 and through of base 36, FIG. 2 where, it connects to a vertically upright passage or hole 42 within a vertically upright post or pipe 44. The pipe 44 is integrally molded to the base 36. Additionally, a medication injection port is formed at 48 within a horizontal pipe 46 as an axial bore cylindrical pipe 46 extends through end wall 34 such that the medication injection port 48 opens to the nebulizer chamber 32. FIG. 2. A plug or seal (not shown) may be inserted within bore 48 to seal off the medication injection port after a sufficient supply of liquid medication is supplied to chamber 32.

A nozzle member indicated generally at 50 which may be of molded plastic, is comprised of a flat plate 52 which supports integrally, a molded hollow cylindrical nozzle 54 which rises from the plate 52 with its axis vertical. The nozzle 54 has an internal diameter which is slightly larger than the outside diameter of pipe 44 and the plate 52 is fixedly mounted on the upper surface 36*b* of base 36 and is spaced slightly therefrom by means of spacers 56, FIG. 2 such that, a horizontal passage is formed at 58 between the bottom surface of plate 52 and the top surface 36*b* of base 36. Further, this passage 58 opens to an annular space 60 defined by the interior surface of nozzle 54 and the exterior surface of the pipe 44. Further, the vertical height of the pipe 44 is less than the vertical height of nozzle 54 such that a small circular sourcė gas and medication mixing chamber 62 is formed between top 44*a* of pipe 44 and the top 54*a* of nozzle 54. The top 54*a* of the nozzle 54 carries cross bars 54*b*, FIG. 1, defining four circumferentially spaced openings 56 leading to the nebulizer chamber 32. The unitary cross bars 54*b* at the top of 54*a*, of the nozzle 54 function as a baffle and the center of the cross overlies a small diameter nozzle opening 42*a* within the top of pipe 44. The area of intersection of the cross bars 54*b* forms a baffle ball 54*c*. against which the source gas G along with any medication, exasperated into a mixing chamber 62, impacts further breaking up the liquid medication into fine droplets and creating a gas and medication particle mist discharging into the chamber 32. Such a gas and medication particles in mist form seeks outlet passage 30 to escape the chamber.

The second principle component of the nebulizer 10 is the detachably connected valved PEEP "T" assembly 14. The valved PEEP "T" assembly 14 in the embodiment of FIGS. 1–3 is constructed as a tube within a tube assembly. A T-shaped based outer tube 70, is formed as an integral molding of, or of an assembly of two pieces of pipe, a main, horizontal pipe 72 of a given diameter, and a shorter length vertical pipe 74. Pipe 74 is of the same diameter adhesively fixed, thermal bonded or otherwise sealably attached to the horizontal pipe 72 at its center and being open thereto. Pipe 74 has an inside diameter which is slightly larger than the outside diameter of outlet tube 28 and which may be permanently fixed or slidably and sealably forced fitted to outlet tube 28 of the nebulizer body 10.

Pipe 74 is provided with an internal bore 76 which opens to a horizontal bore 78 of the horizontal pipe 72. Annular grooves 80 are formed internally at each end of the horizontal pipe 72 within bore 78 which grooves 80 receive respectively, O-rings 82 of a diameter in excess of the depth of the groove 80 so that a portion of the O-rings 82 project outwardly into the regularly beyond the bore 78 inner surface of the horizontal tube 72. A rotary valve control tube or inner tube 84 of the valved PEEP "T" assembly 14 has an axial length which is in excess of the length of the horizontal pipe 72 of the outer tube 70. Preferably, outer tube 84 has a radially enlarged, short length part 94 with an outside diameter equal to that of horizontal pipe 72 of outer tube 70. Outer tube 84 has a radial wall, at part 94, which is substantially thicker than that of horizontal pipe 72 such that the inner diameter of outer tube 84 is somewhat less than that of the inner diameter of the horizontal pipe 72. Over a substantial portion 86 of its axial length, the outer tube 84 is of reduced diameter, such that the outside diameter of portion 86 of tube 84 is just less than the inside diameter of horizontal pipe 72 of outer tube 70. As a result, the inner tube 84, portion 86 is readily, slidably insertable within the interior of the horizontal pipe 72 and in which case, the inside diameter of the O rings 82 is less than the diameter of the reduced diameter portion 86 of outer tube 84, FIGS. 1 and 2. Further, a radial opening or hole 88 of circular form, is formed within reduced diameter portion 86 of the outer tube 84 which hole 88 is alignable with the bore 76 of the vertical pipe 74 of the valved PEEP "T" assembly 14 outer tube 70.

Further, preferably limits are provided for the rotation of inner tube 84 within the horizontal pipe 72 of outer tube 70. A tab 90 projects longitudinally beyond the left end of the horizontal pipe 72 and is received within an annular recess 92 formed within the end of the larger diameter portion 94 of the inner tube 84. Tab 90 function as a stop, preventing rotation of the inner tube 84, beyond approximately 90°, in either direction by abutment of tab 90 with shoulders 96 and 98 thereby defining, respectively. ON and OFF positions for the valved "T" assembly 14.

With the inner tube 84 rotated counterclockwise. FIG. 1 to a position where shoulder 98 abuts the stop or tab 90, the circular hole 88 within the side wall of tube 84 is aligned fully with the bore 76 of vertical pipe 74. Rotation of inner tube 94 from that position, clockwise to the extent where shoulder 96 abuts the other side of the longitudinally projecting stop 90, results in shifting of hole 88 to a position where the bore 100 of inner tube 84 is cut off from the bore 100 of 76 of the short vertical height pipe 74 of valved "T" member outer tube 70. Preferably, four rubber O rings 82 are provided within respective annular grooves 80 at various, longitudinally spaced positions i.e. two at opposite ends of the horizontal tube 72 and two adjacent opposite sides of the circular hole 88 within the reduced diameter portion 86 of the flow control tube 84. The O rings 82 seal off the space between the inner tube 84 and the horizontal pipe 72 of outer tube 72 of assembly 14. Such seals should be airtight seals. Of course, the sealing arrangement may be modified and indeed it is possible to match that the outer diameter of section 86 of the inner tube 84 to the inside diameter of the horizontal pipe outer tube 70, such that O ring seals may be dispensed without leakage of fluid.

With the assembly as shown in FIG. 2, either a continuous supply of liquid medication as per arrow M. FIG. 1 may be supplied to the interior of the nebulizer body 12 via medication injection port 48, or an intermittent supply, as desired. The slope of bottom wall portion 24b and the slope of the laterally opposed slide walls 20. 22 of the nebulizer body 12 are such that any remaining small amount of liquid medication M seeks the space 58 between the bottom of plate 52 and the top 36b of base 36, passing about the circumferentially separate spacers 56 maintaining the plate 52 apart from the base 36. A supply of a source gas under pressure, as per arrow G. FIG. 2 to the small diameter bore 40 of source gas supply tube 38 causes, the escape of such a gas through the small diameter nozzle opening 42a at the upper end of the nozzle 44. The flow of such gas through the mixing chamber 62 aspirates the liquid medication M upwardly through the annular space or passage 60 and mixes the medication M with the source gas G in mixing chamber 62 and, breaks the liquid into medication particles. i.e. droplets. The droplets impinge in that mixture against the crossbars 54b, particularly the baffle ball 54c at the intersection thereof. Under this action, a mist of a source gas and medication particles fills the balance of the chamber 32 above the level L of the liquid medication. The source gas G and the medication M particles seek escape through outlet pipe 28 which connects to the valved PEEP "T" assembly 14 via vertical pipe 74. Assuming that the flow control inner tube 84 is rotated to the ON position, the nebulized medication gas mixture then passes, in the inhalation phase of the ventilator cycle, through the interior of the inner tube 84.

After a particular dosage of medication M is carried to the patients via a ventilation circuit tube or hose connected at an end of the inner tube 84 of assembly 14, the inner tube 84 is rotated one half turn shifting shoulder contact with tab or stop 90 from shoulder 98 to that of shoulder 96. This action prevents any water condensing on the elements of the ventilation circuit or the nebulizer and valve "T" structure from draining down into the nebulizer casing 16 which forms a bowl for the liquid medication M prior to aspiration. Particle size and flow rate of the medication is controlled partially by rotation of the inner tube 84 relative to outer tube 70 of the valved PEEP "T" assembly outer tube 70. Because of the compactness of the nebulizer 10, the nebulizer may be placed proximate to the patient, with less rainout of the medication in the tubing occurring and a larger content of the medication being in mist form delivered to the patient's airways. The horizontal tubing (not shown) for supplying respectively, the medication via port 48 in pipe 46, and the source gas via pipe 38 and passage 40 is less likely to kink and to shut off or reduce the flow of these constituents to the nebulizer body 12. Inclination of the elongated nebulizer body casing 16 from horizontal has little effect since the sloping sides 20, 22 and sloping bottom 24b tend to insure that the liquid medication, flows to the area of nozzle 44 and the aspiration passage 58, 60 defined by members 36, 52,; and 44, 54.

Turning to FIGS. 4 and 5. a somewhat different form of valved PEEP "T" assembly 114 is illustrated and may be mounted to the outlet pipe 28 of nebulizer body 12 in lieu of assembly 14 in FIGS. 1 and 2. In that case, the valved "T" PEEP assembly 114 is formed of a T-shaped outer tube, indicated generally at 170. A short length vertical pipe 174 is molded into or adhesively bonded, or thermal bonded to the side of the elongated horizontal pipe 172 intermediate of its ends, with the bore 176 thereof open to the bore 178 of the short length horizontal pipe 172.

In this case, however, there is rotatably mounted within bore 178 of the horizontal pipe 172, a hollow. spherical valve member 200 sandwiched between hollow annular seats 208 on the top and bottom of the spherical valve member and integral with or fixed to the interior wall of the horizontal pipe 172. Valve member 200 has one bore 202 passing completely therethrough from one side to the diametrically opposite side, and in addition, an intersecting right angle bore 204. Bore 204 extends through one side of the spherical member, the opposite side of the sphere being blocked off by a solid portion 206 of the spherical rotatable valve member 200. Further, a valve operator 210 is rotatably mounted to the side of the horizontal pipe, having a shaft portion 216 which projects through an opening 212 within the side wall tube 172 and which is fixed to the spherical valve member 200. A handle 214 is integral with a shaft 212 and projects exterior of the horizontal pipe 172, and extends at right angles thereto, parallel to pipe 172, such that, by grasping the handle 214, the spherical valve member 200 may be rotated about a horizontal axis A. By rotating the Valve 180° from the position shown in FIG. 5, the solid wall 206 is aligned with the bore 176 of the short vertical pipe 174 to close off fluid communication between the vertical pipe 174 and the horizontal pipe 172 of the "T" assembly 114 outer tube 170. Under such conditions, there is no communication between the ventilation circuit and the nebulizer chamber 36 via the valved "T" PEEP assembly 114. However, under conditions shown in FIGS. 4 and 5, communication is open so that the medication in mist form is properly fed into the airstream to the patient via such circuit. After sufficient medication M reaches the patient, the valve member 200 may be readily shifted to its closed condition thereby preventing any water from draining into the nebulizer chamber preventing contamination of that chamber.

From the above description of the preferred embodiments of the invention, it is apparent that the parts, with the exception of the O rings 82 and as seats and/or seals 208 in the modified valved "T" assembly of FIGS. 4 and 5, may be readily made of molded plastic. The nebulizer is therefor formed of relatively few parts, operates efficiently, for both aspects of particle size control and valve on/off operation and may be readily positioned close to the body of the patient and in proximity to the airways of the patient.

It will be understood that modifications may be made within the scope of the appendant claims, without the parting from the principle or sacrificing the advantages of the invention as described above and as illustrated in the drawings.

What is claimed is:

1. A horizontally elongated hollow, shallow nebulizer body having vertically spaced top and bottom walls, at least one vertical end wall and laterally opposed side walls joining said top wall to said bottom wall, said body being generally trapezoidal in side configuration, a horizontal source gas supply tube mounted to said at least one vertical end wall and opening internally thereof, a vertical pipe within said body, being connected to said source gas supply tube and terminating at an upper end in a reduced diameter nozzle opening, an inverted cup-like hollow cylindrical nozzle member having an inner diameter in excess of the outer diameter of said vertical pipe and concentrically surrounding said pipe and forming an annular liquid aspirating passage therebetween, said vertical pipe terminating at an upper end in an end wall extending across the upper end of said vertical pipe and being axially spaced above the end of said pipe to form a cylindrical mixing chamber between the upper end of said vertical pipe and the upper end of said nozzle member, at least one outlet opening in said nozzle member upper end wall, opening outwardly to the interior of said nebulizer body, said nebulizer body including means for supplying a liquid medication to the interior of said body and said shallow, hollow nebulizer body bottom wall including an upwardly oblique portion extending from the side of said vertical pipe and said inverted cup-like hollow, cylindrical nozzle member toward said top wall such that any liquid medication within said body tends to accumulate in the vicinity of said annular aspirating passage, said top wall including a cylindrical vertical outlet opening to the interior of said hollow nebulizer body and projecting upwardly therefrom, and wherein, said nebulizer further comprises a valved "T" hollow tube assembly comprising a horizontally elongated outer pipe, and a short length vertical pipe fixed thereto at one side thereof, and a cylindrical hole within the side of a said horizontal pipe sized to the bore of the short length vertical tube and opening thereto, and an adjustable valve member mounted internally of the horizontally elongated outer pipe, and selectively moveable to close off and open, the connection between the bore of the elongated horizontal pipe and the bore of the short length vertical pipe whereby, with liquid medication within said hollow nebulizer body, and a supply of a source gas to the horizontal source gas supply tube, passage of said gas through said vertical pipe interior of said body causes aspiration of liquid through said inverted cup-like hollow cylindrical nozzle member annular passage and mixing of the liquid medication and the source gas within said chamber, such that by opening and closing the valve of said valved "T" assembly, a mist of medication particles and said source gas is formed within said hollow body for entry into the bore of said elongated horizontal pipe for passage selectively through ventilator tubing into interior airways of a patient by a ventilation circuit including said nebulizer with said valved "T" assembly.

2. The nebulizer as claimed in claim 1, wherein said vertical end wall further comprises a horizontal pipe and extending through said end wall and having an axial bore therein, forming a medication injection port open to the interior of the nebulizer body and oriented parallel to said source gas supply, such that flexible tubes connected to said source gas supply tube and said horizontal pipe, are virtually free of kinking, thus preventing failure of source gas or liquid medication flow to the interior of the hollow nebulizer body during operation of the nebulizer.

3. The nebulizer as claimed in claim 1, wherein, the upper end wall of said nozzle body includes a pair intersecting cross bars forming four circumferentially spaced outlets openings therein, the intersection of said two cross bars forming a ball aligned with the reduced diameter nozzle opening of said vertical pipe such that, liquid medicament aspirated into the mixing chamber impinges against the crossed bars at said ball, to break up the liquid into fine droplets thereby forming a fine mist of source gas and medication droplets which tend to fill the interior of the shallow, hollow nebulizer body.

4. The nebulizer as claimed in claim 1, wherein, said nebulizer body is in the form of an open ended molded plastic casing having a short length horizontal bottom wall portion, said vertical end wall is sealed about the edges thereof to edges of open ends of the laterally opposed side walls, said top and bottom walls at the end of the horizontal bottom wall portion remote from said upwardly oblique bottom wall portion.

5. The nebulizer as claimed in claim 1 wherein said vertical end wall, to the side thereof exterior of said nebulizer body, includes a rectangular parallelepiped base, projecting horizontally therefrom and being integral therewith and having opposite sides sized to the lateral distance between the laterally opposed side walls of said nebulizer body, said base is insertably positioned between said body side walls, and wherein, said horizontal source gas supply tube has a bore, extending horizontally through a portion of said base, and opening to the bore of said vertical pipe fixed to said base.

6. The nebulizer as claimed in claim 5, wherein the laterally opposite side walls of said nebulizer body, are inclined upwardly and inwardly, the sides of said vertical end wall are also inclined upwardly and inwardly such that the vertical end wall is of trapezoidal shape, conforming to a trapezoidal transverse cross-sectional configuration of said nebulizer body casing.

7. The nebulizer as claimed in claim 1 wherein, said inverted, cup-like hollow cylindrical nozzle member terminates at a lower end thereof in an integral, flat horizontal plate sized to said vertical end wall base and facing the same, and wherein spacer means are provided between said inverted cup-like hollow cylindrical nozzle member and one of said vertical pipe and said base and defining a horizontal passage for flow of liquid medicant to the bottom of said annular aspirating chamber between said vertical pipe and said hollow cylindrical nozzle member.

8. The nebulizer as claimed in claim 1, wherein said valved "T" assembly comprises a T-shaped outer tube consisting of a elongated horizontal pipe and a short length vertical pipe integrated to the side of said elongated horizontal pipe and having a bore thereof open to a bore of said elongated horizontal pipe, and a hollow valve member internally of said hollow valve member having at least one opening therein within a side thereof alignable with an opening within the side of said horizontal pipe aligned with the bore of said short length vertical pipe for selectively communicating the interior of the elongated horizontal pipe with the bore of said short length vertical pipe, and wherein said short length vertical pipe of the hollow T member is fixedly sealably coupled to the end of said outlet pipe of said nebulizer body projecting upwardly above the top of that body.

9. The nebulizer as claimed 8 wherein, said rotatable body comprises an elongated horizontal inner tube, said inner tube including a portion at one end of a reduced diameter, sized slightly less than the inside diameter of the elongated horizontal pipe of said T-shaped outer tube, and being slidably inserted therein and wherein said reduced diameter portion of said outer tube has a radial hole sized to the diameter of the bore within the side wall of said elongated horizontal pipe and being rotatably alignable therewith so as to effect selectively, communication between the bore of said inner tube, and the bore of short length vertical pipe of said T-shaped outer tube.

10. The nebulizer as claimed in claim 9, wherein said inner tube includes a radially enlarged portion at the end thereof opposite said radially enlarged portion, and being abutable with one end of said elongated horizontal pipe of said T-shaped outer tube, wherein, said elongated horizontal pipe includes a longitudinally projecting tab at the end thereof proximate to said inner tube, wherein said radially enlarged portion of said inner tube, includes an arcuate recess over a circumferential extent of approximately 90° and forming circumferentially opposed longitudinally projecting shoulders and wherein, said inner tube is mounted within said elongated horizontal pipe of said T-shaped outer tube with said tab positioned within said arcuate recess whereby, said tab contacts respective shoulders by rotation of the inner tube relative to the outer T tube to valve OFF and ON positions at respective shoulders.

11. The nebulizer as claimed in claim 8, wherein said rotatable hollow valve member comprises a hollow spherical valve member, said spherical valve member including a first bore extending through said sphere diametrically from one side to the other and a second bore opening at right angles to said first bore from one side of said sphere only, and wherein, said hollow spherical valve member is positioned within said bore of said elongated horizontal tube, and supported for rotation about a axis extending horizontally through said elongated horizontal tube, and at right angles to the axis of said short length tube, such that, by rotation of said hollow spherical member through an angle of 180°, from a full ON position with said first bore aligned with the axis of the elongated horizontal pipe, and the second bore aligned with the axis of the short length vertical pipe, communication between the bore of the elongated horizontal pipe and the short length vertical pipe is cut off, with said hollow sphere at a second OFF position with a closed portion of said hollow spherical valve member spanning across the end of said short length vertical pipe thereby sealing off the bore of such short length vertical pipe from that of said elongated horizontal pipe.

12. The nebulizer as claimed in claim 11, wherein an L shaped actuator is rotatably mounted to the side of said elongated horizontal pipe, and said actuator includes a shaft portion extending transversely through said elongated horizontal pipe and being coupled to said hollow spherical valve member, and a handle integral with said shaft, exterior of said elongated horizontal pipe, and extending 90° to the axis of said shaft.

* * * * *